(12) United States Patent
Herweijer et al.

(10) Patent No.: US 7,781,415 B2
(45) Date of Patent: *Aug. 24, 2010

(54) PROCESS FOR DELIVERING SIRNA TO CARDIAC MUSCLE TISSUE

(75) Inventors: Hans Herweijer, Madison, WI (US); Julia Hegge, Monona, WI (US); Jon A. Wolff, Madison, WI (US); David L. Lewis, Madison, WI (US)

(73) Assignee: Roche Madison Inc., Madison, WI (US)

( * ) Notice: Subject to any disclaimer, the term of this patent is extended or adjusted under 35 U.S.C. 154(b) by 442 days.

This patent is subject to a terminal disclaimer.

(21) Appl. No.: 10/770,588

(22) Filed: Feb. 3, 2004

(65) Prior Publication Data

US 2004/0157790 A1 Aug. 12, 2004

Related U.S. Application Data

(60) Provisional application No. 60/445,634, filed on Feb. 7, 2003.

(51) Int. Cl.
*A61K 48/00* (2006.01)
(52) U.S. Cl. ............... 514/44; 536/24.5; 536/24.31; 536/24.1
(58) Field of Classification Search .............. 435/6, 435/91.1, 91.3, 325, 375; 536/23.1, 24.5, 536/24.3, 24.31, 24.33; 514/44
See application file for complete search history.

(56) References Cited

U.S. PATENT DOCUMENTS

| | | | | |
|---|---|---|---|---|
| 5,922,687 A * | 7/1999 | Mann et al. | ............... | 514/44 |
| 6,159,946 A | 12/2000 | Zalewski et al. | | |
| 6,379,966 B2 * | 4/2002 | Monahan et al. | ............ | 435/455 |
| 6,627,616 B2 * | 9/2003 | Monahan et al. | ............... | 514/44 |
| 2002/0132788 A1 * | 9/2002 | Lewis et al. | ............... | 514/44 |
| 2002/0172663 A1 | 11/2002 | Palasis | | |
| 2003/0092180 A1 * | 5/2003 | Lewis et al. | ............... | 435/455 |
| 2003/0153519 A1 * | 8/2003 | Kay et al. | ............... | 514/44 |

OTHER PUBLICATIONS

Caplen NJ. RNAi as a Gene Therapy Approach. Expert Opinon. Biol. Thera. (2003) vol. 3(4) 575-586. Ashley Publications Ltd.*
Von Der Leyen et al. A Pressure Mediated Nonviral Method for Efficient Arterial Gene and Oligonucleotide Transfer. Human Gene Therapy (1999). vol. 10:2355-2364. Mary Ann Liebert, Inc.*
Paroo et al. Challenges for RNAi in vivo. Trends in Biotechnology (2004), vol. 22(8) 309-394. Elsevier.*
Novina, et al. The RNAi revolution. Nature (2004), vol. 430: 161-164. Nature Publishing Group.*
Ma et al. Focal arterial transfene expression after local gene delivery. Can J Cardiol (2001) vol. 17(8):873-883. Pulsus Group.*
Lewis et al. Efficient delivery of siRNA for inhibition of gene expression in postnatal mice. Nature Genetics (2002), vol. 32:107-108. Nature Publishing Group.*
Adams, A. RNA therapeutics enter clinical trials. Scientist (2005), vol. 19:Issue 1. Institute for Scientific Information.*
Green et al. Antisense oligonucleotides: an evolving technology for the modulation of gene expression in human disease. J Am Coll Surg (2000), vol. 191:105. Elsevier.*
Jen et al. Suppresion of Gene Expression by Targeted Disruption of Messenger RNA: Available Options and Current Strategies. Stem Cells (2000), vol. 18:307-319. AlphaMed Press.*
Liu et al. Hydrodynamic-based transfection in animals by systemic administration of plasmid DNA. Gene Therapy (1999), vol. 6:1258-1266. Stockton Press.*
Hammond et al. Post-transcriptional gene silencing by double-stranded RNA Nature, 2001, vol. 2, 110-119. MacMillan Magazines Ltd.*
Invasiveness. (n.d.). The American Heritage® Dictionary of the English Language, Fourth Edition. Retrieved Dec. 14, 2006, from Dictionary.com website: http://dictionary.reference.com/browse/invasiveness.*
Magovern CJ et al. "Direct in vivo gene transfer to canine myocardium using a replication-deficient adenovirus vector." Ann Thorac Surg. 1996 vol. 62 No. 2 pp. 425-433.
March L et al. "Efficient in Vivo Catheter-Based Pericardial Gene Transfer Mediated by Adenoviral Vectors." Clinical Cardiology; 1999 vol. 22, 123-129.
Maurice JP et al. "Enhancement of Cardiac Function After Adenoviral-Mediated in Vivo Intracoronary B2-Adrenergic Receptor Gene Delivery." The Journal of Clinical Investigation; 1999 vol. 104, No. 1, pp. 21-29.
Schumacher B et al. "Induction of neoangiogenesis in ischemic myocardium by human growth factors: first clinical results of a new treatment of coronary heart disease." Circulation; 1998 vol. 97 No. 7 pp. 645-650.
Sharp PA. "RNA interference-2001." Gene and Development; 2001 vol. 15 pp. 485-490.
Takeshita S et al. "Therapeutic angiogenesis. A single intraarterial bolus of vascular endothelial growth factor augments revascularization in a rabbit ischemic hind limb model." J Clin Invest; 1994 vol. 93 No. 2 pp. 662-670.
Tuschl T et al. "Targeted mRNA degradation by double-stranded RNA in vitro." Genes and Development; 1999 vol. 12 pp. 3191-3197.
Vale Pr et al. "Catheter-Based Myocardial Gene Transfer Utilizing Nonfluoroscopic Electromechanical Left Ventricular Mapping." Journal of the American College of Cardiology; 1999 vol. 34 No. 1, pp. 246-254.
Wright MJ et al. "β-Galactosidase Staining Following Intracoronary Infusion of Cationic Liposomes in the In Vivo Rabbit Heart is Produced by Microinfarction Rather Than Effective Gene Transfer: A Cautionary Tale." Gene Therapy; 1998 vol. 5 pp. 301-308.

(Continued)

*Primary Examiner*—Kimberly Chong
(74) *Attorney, Agent, or Firm*—Kirk Ekena (57) ABSTRACT

A process for delivering a polynucleotide to a cardiac tissue cell in a mammal is described, comprising introducing a composition consisting of a polynucleotide into a blood vessel and increasing permeability of the blood vessel to the polynucleotide. The polynucleotide can be a small interfering RNA or microRNA and inhibit gene expression in the cell.

16 Claims, 5 Drawing Sheets

OTHER PUBLICATIONS

Acsadi G et al. "Direct Gene Transfer and Expression Into Rat Heart in Vivo." The New Biologist; 1991 vol. 3 No. 1 pp. 71-81.

Aoki M et al. "Efficient in vivo gene transfer into the heart in the rat myocardial infarction model using the HVJ (Hemagglutinating Virus of Japan)—liposome method." J Mol Cell Cardiol; 1997 vol. 29 No. 3 pp. 949-59.

Barr E et al. "Efficient Catheter-Mediated Gene Transfer Into the Heart Using Replication-Defective Adenovirus." Gene Therapy; 1994 vol. 1 pp. 51-58.

Baumgartner I et al. "Constitutive expression of phVEGF165 after intramuscular gene transfer promotes collateral vessel development in patients with critical limb ischemia." Circulation; 1998 vol. 97 No. 12 pp. 1114-1123.

Donahue JK et al, "Acceleration of Widespread Adenoviral Gene Transfer to Intact Rabbit Hearts by Coronary Perfusion With Low Calcium and Serotonin." Gene Therapy; 1998 vol. 5 pp. 630-634.

Elbashir SM et al. "Duplexes of 21-nucleotide RNAs mediate RNA interference in cultured mammalian cells." Nature; 2001 vol. 211 pp. 494-498.

Elbashir SM et al. "RNA interference is mediated by 21- and 22-nucleotide RNAs." Genes and Development; 2001 vol. 15 pp. 188-200.

Gal D et al. "Direct Myocardial Transfection In Two Animal Models." Laboratory Investigation 1993; vol. 68, No. 1; p. 18.

Giordano FJ et al. "Intracoronary gene transfer of fibroblast growth factor-5 increases blood flow and contractile function in an ischemic region of the heart." Nat Med; 1996 vol. 2 No. 5 pp. 534-539.

Hajjar RJ et al. "Modulation of Ventricular Function Through Gene Transfer in Vivo." Proc Natl Acad Sci USA; 1998 vol. 95, pp. 5251-5256.

Lazarous DF et al. "Adenoviral-Mediated Gene Transfer Induces Sustained Pericardial VEGF Expression in Dogs: Effect on Myocardial Angiogenesis." Cardiovascular Research; 1999 vol. 44, pp. 294-302.

Lin H et al. "Expression of Recombinant Genes in Myocardium in Vivo After Direct Injection of DNA." Circulation; 1990 vol. 82 No. 6 pp. 2217-2221.

Losordo D et al. "Gene Therapy for Myocardial Angiogenesis." Circulation; 1998 vol. 98 pp. 2800-2804.

Mack CA et al. "Biologic bypass with the use of adenovirus-mediated gene transfer of the complementary deoxyribonucleic acid for vascular endothelial growth factor 121 improves myocardial perfusion and function in the ischemic porcine heart." J Thorac Cardiovasc Surg; 1998 vol. 115 No. 1 pp. 168-176.

* cited by examiner

PROCESS FOR DELIVERING SIRNA TO CARDIAC MUSCLE TISSUE

CROSS-REFERENCE TO RELATED APPLICATIONS

This application claims benefit of prior U.S. Provisional Application Ser. No. 60/445,634 filed on Feb. 7, 2003.

FIELD

The present invention generally relates to inhibiting gene expression in vivo. Specifically, it relates to inhibiting gene expression in heart muscle tissue by delivery of polynucleotides.

BACKGROUND OF THE INVENTION

The delivery of genetic material as a therapeutic promises to be a revolutionary advance in the treatment of disease. Although, the initial motivation for gene therapy was the treatment of genetic disorders, it is becoming increasingly apparent that gene therapy will also be useful for the treatment of a broad range of acquired diseases such as cancer, infectious disorders (AIDS), heart disease, arthritis, and neurodegenerative disorders (Parkinson's and Alzheimer's). In addition to providing a therapeutic benefit, nucleic acid delivery is also beneficial for the study of gene function and drug interaction. Not only can functional genes be delivered to repair a genetic deficiency, but polynucleotides can also be delivered to inhibit gene expression. Inhibition of gene expression can be affected by antisense polynucleotides, siRNA mediated RNA interference and ribozymes. Transfer methods currently being explored included viral vectors and physical-chemical methods.

RNA interference (RNAi) describes the phenomenon whereby the presence of double-stranded RNA (dsRNA) of sequence that is identical or highly similar to a target gene results in the degradation of messenger RNA (mRNA) transcribed from that target gene [Sharp 2001]. It has been found that RNAi in mammalian cells is mediated by short interfering RNAs (siRNAs) of approximately 21-25 nucleotides in length or microRNAs [Tuschl et al. 1999; Elbashir et al. 2001]. The ability to specifically inhibit expression of a target gene by RNAi has obvious benefits. For example, RNAi could be used to study gene function. In addition, RNAi could be used to inhibit the expression of deleterious genes and therefore alleviate symptoms of or cure disease. SiRNA/microRNA delivery may also aid in drug discovery and target validation in pharmaceutical research.

A basic challenge in gene therapy, whether for therapeutic or research purposes, is to develop approaches for delivering genetic material to the appropriate cells in a way that is specific, efficient and safe. This problem of 'drug delivery', where the drug is a polynucleotide, is particularly challenging. If polynucleotides are appropriately delivered they can potentially lead to amelioration of a disease or condition. Delivery of polynucleotides to cells in vivo is also useful in basic research: in the study of cell physiology, gene function, drug discovery and interaction, disease, and infection.

Gene therapy promises to be a significant advance in the treatment of both acquired and genetic diseases at the most fundamental levels of pathology. Specifically, the development of gene transfer methods into the heart is attractive given that coronary artery disease is the leading cause of morbidity and mortality in the United States. Despite advances in the prevention and treatment of this disorder there remains a large population of patients who are not optimal candidates for percutaneous or surgical revascularization, usually because of severe distal vessel disease or previous failed revascularization procedures. Coronary collateral development is an important adaptive response of the ischemic heart in this situation, but often the collateral circulation is inadequate and results in severe angina pectoris despite maximal medical therapy. A new strategy to treat these often disabled patients involves the local delivery of vascular cytokines to induce new blood vessel growth (neoangiogenesis) in the ischemic myocardium. Alternatively, nucleic acids (e.g., siRNA or siRNA expression vectors) can be delivered that down regulated repressors of angiogenesis. It has been recognized that gene therapy could play a major role in neovascularization approaches.

A variety of techniques has been developed to transfer polynucleotides into the heart. These techniques have principally involved adenovirus vectors, which can be injected directly or intravenously, and plasmid DNA vectors injected directly into the heart tissue. The first reports of successful non-viral in vivo gene delivery to the heart used direct injection of plasmid DNA vectors [Lin et al. 1990; Acsadi et al. 1991]. High levels of β-galactosidase reporter gene expression were measured several days after injection of plasmid DNA solutions. Expression appeared to be highly localized to the site of injection. Adenoviral vectors have been used extensively for gene transfer into cardiac muscle. Barr et al. found transduction levels of 10-32% after intracoronary installation of virus. However, expression was also found in endothelial cells and the presence of the viral genome was detected in other organs [Barr et al. 1994]. Many of these gene therapy studies were aimed at transducing vascular endothelial cells to prevent restenosis following angioplasty. The injection of adenoviral vectors into the portal or systemic circulatory systems leads to high, but transient levels of foreign gene expression in several organs (liver, lung, etc.). Immune responses directed against the viral coat proteins and proteins expressed from the viral genome are another problem associated with viral delivery. Also, adenoviral transduction of infarcted heart tissue has been less efficient than normal tissue. Decreased transduction efficiency in diseased heart tissue could be a problem for viral gene therapy approaches for ischemic heart disease.

Until recently, the direct injection of plasmid DNA into the heart has mainly been used to benefit basic researchers investigating transcriptional regulation of cardiac specific genes. Isner and co-workers [Takeshita S et al. 1994] have pioneered the in vivo delivery of genes that result in neovascularization of ischemic muscle. In a breakthrough gene therapy study, they demonstrated significant formation of new vessels, enhanced distal flow, and clinical benefit in patients with ischemic limbs following injection of plasmid DNA expressing the human vascular endothelial growth factor (hVEGF) gene [Baumgartner I et al. 1998]. This same hVEGF-expressing plasmid has been injected into ischemic heart tissue in humans [Losordo DW et al. 1998]. Preliminary results are very promising, with significant reduction in reported angina, and improved Rentrop score in 5 of 5 patients.

In vivo transfection of plasmid DNA complexed with liposomes after direct injection into heart muscle resulted in localized expression of reporter genes [Aoki M et al. 1997]. While highly effective in vitro, liposome-complexed plasmid DNA particles generally have been of limited success in vivo. Systemic delivery of both adenoviral vectors and liposome-plasmid DNA complexes provides much greater efficiency of delivery into liver and lung than into heart, making these strategies unattractive for cardiac gene therapy.

Using a porcine chronic coronary occlusion model, it was shown that single coronary injections of a replication-defective adenovirus vector expressing fibroblast growth factor-5 (FGF-5) resulted in improved regional myocardial blood flow and histological evidence of increased capillary number [Giordano F J et al. 1996]. Stress-induced regional contractile dysfunction was documented by echocardiography after coronary occlusions in this study. Importantly, this pacing-induced regional wall motion abnormality was completely normalized within two weeks after intracoronary FGF-5 gene transfer and the amelioration of stress-induced myocardial ischemia persisted for at least 12 weeks. Again using the porcine model chronic coronary occlusion model, Mack et al. 1998 showed similar amelioration of pacing-induced myocardial ischemia and improvement in blood flow after multiple direct intramyocardial injections of a replication-defective adenovirus expressing $hVEGF_{121}$.

The intravascular delivery of plasmid DNA has been shown to be highly effective for gene transfer into liver, skeletal and cardiac muscle (U.S. application Ser. No. 09/330,909, U.S. Pat. No. 6,627,616). Non-viral vectors are inherently safer than viral vectors, have a reduced immune response induction and have significantly lower cost of production. Furthermore, a much lower risk of transforming activity is associated with non-viral polynucleotides than with viruses.

SUMMARY OF THE INVENTION

In a preferred embodiment, a process is described for delivering a polynucleotide to a cardiac tissue cell in a mammal, comprising: introducing the polynucleotide in a solution into a vessel of the heart, increasing the permeability of the vessel to the polynucleotide and delivering the polynucleotide to the cardiac tissue cell. A preferred polynucleotide is an siRNA, microRNA or functional equivalent.

In a preferred embodiment we describe a process for inhibiting gene expression in mammalian heart muscle cells in vivo comprising: injecting a solution containing siRNA into a vessel of the heart via a catheter. Balloon catheters can effectively define the bed size by blocking the vessel behind the solution instillation site.

In a preferred embodiment, we describe an in vivo process for the delivery of polynucleotides to cardiac muscle cells in a mammal comprising: injecting the polynucleotides in a solution into a vessel, wherein the volume and rate of the injection results in increasing permeability of the vessel to provide for delivery of the polynucleotide to cardiac cells outside the vessel. Increasing vessel permeability may further comprise blocking the flow of fluid through the vessel. The solution may contain a compound or compounds which may or may not associate with the polynucleotide and may aid in delivery. The polynucleotide may be an RNA function inhibitor selected from the list consisting of: siRNA, dsRNA, microRNA, antisense RNA and ribozyme.

In a preferred embodiment a process is described for gene therapy, comprising: inserting a polynucleotide into a vessel of the heart, increasing the permeability of the vessel, and delivering the polynucleotide to a cardiac muscle cell wherein the polynucleotide inhibits expression of a gene in the cell.

BRIEF DESCRIPTION OF THE FIGURES

FIG. 1. (A) Single balloon catheters for nucleic acid delivery: A single balloon catheter generally comprises a two-lumen catheter, in which one lumen is used to inflate or deflate the balloon and the other lumen for other purposes, e.g., guidewires, delivery of fluids, intravascular pressure measurements. Such catheters are available in many different sizes (diameter and length), to accommodate applications in different sized and localized vessels. In one embodiment, the balloon is located near the tip of the catheter. In inflated condition, the balloon will fix the catheter in place in the targeted vessel, and prevent flow of fluid, delivered through a lumen exiting distal to the balloon, in the proximal direction (back along the catheter). (B) In another embodiment, the inflated balloon can restrict fluid delivery to the proximal region, where the fluid delivery lumen opens proximal to the balloon.

DETAILED DESCRIPTION OF THE INVENTION

A minimally invasive and clinically viable in vivo system for delivery of naked polynucleotides or polynucleotides combined with transfection reagents to a heart is described in this specification. Under appropriate conditions, the intravascular delivery of poly-nucleotides into coronary vessels results in efficient delivery of polynucleotides to heart muscle cells. A retrograde transvenous approach or an arterial route can be used to deliver polynucleotides to myocardial beds supplied by occluded coronary arteries. If the polynucleotides are effective in inhibiting specific gene expression, expression of said gene in the heart muscle cell is inhibited.

The delivery of polynucleotides to the heart is described using injection of a solution containing the polynucleotides into coronary arteries or veins. For the injection, percutaneous transluminal coronary angioplasty (PTCA) catheters can be advanced into the coronary venous system from a peripheral vessel. In a preferred embodiment, double lumen balloon catheters are positioned into coronary veins from peripheral vessels and polynucleotide solutions are injected under pressure to transfect cardiac muscle cells. We further describe an injection system that allows for automated regulation of injection speed and volume correlated to the pressure in the injected vessel. Coronary angioplasty catheters are used to simultaneous inject fluids into the selected coronary bed and measure the intracoronary venous hydrostatic pressure during and after injection. Polynucleotide delivery is optimized and toxicity (tissue damage) is minimized by varying the volume of the polynucleotide-containing solution and the speed of injection.

We have shown efficient gene transfer into cardiac muscle cells following injection of plasmid DNA solutions into coronary arteries and veins in pig hearts (U.S. application Ser. No. 09/330,909, incorporated herein by reference). Luciferase reporter genes were used to assess total foreign gene expression in the heart tissue and the reporter gene LacZ (expressing β-galactosidase) to determine the percentage and type of cells that express plasmid DNA at several time points following injection. Similar high levels of expression were measured following catheter-based polynucleotide delivery. These results suggest that the treatment of myocardial ischemia in patients with coronary artery disease using this method is feasible. An advantage of this method over direct interstitial injection of polynucleotide into the heart is that a complete (ischemic) bed can be targeted. Direct interstitial injection results only in very localized gene transfer and expression. In contrast, intravascular delivery of polynucleotides can result in more widespread cardiac gene expression. We now show that polynucleotides for inhibiting gene expression in cardiac cells can be successfully delivered via intravascular injection.

Adenoviral transduction of infarcted heart tissue is less efficient than transduction of normal tissue. In contrast, using our described delivery procedure, delivery of non-viral polynucleotides to heart tissue appears to more efficient in infarcted heart tissue. Therefore, the described process allows for more optimal delivery of polynucleotides to diseased heart. Furthermore, when injected intravascularly, adenoviral vectors and other viral vectors may efficiently transduce other cells, such as endothelial cells, in addition to cardiac muscle cells. The transduction of distant organs after intravascular adenovirus delivery is also a major safety concern. A broad spectrum of affected cell types is undesirable for many heart gene therapy applications. Using the describe process, there is much less of a risk for polynucleotide delivery non-heart tissues since the targeted tissue is determine by the vessel into which the polynucleotide is injected.

We have developed an intravascular process for the delivery of biologically active compounds to extravascular heart tissue cells. Polynucleotides are injected into a vessel for delivery of the polynucleotides to extravascular cells supplied or drained by the vessel. A key advancement is the enhanced delivery to a larger and more even distribution of cells than is achieved by direct parenchymal injections. More efficient delivery is achieved by increasing permeability of vessels. Vessel permeability and extravascular fluid volume is increased by one or more of the following: using a sufficient volume of injection solution, injecting the solution at an appropriate rate, impeding fluid flow into and/or out of the target tissue during the process, and increasing permeability of the vessel wall.

Many blood vessels naturally contain pores or fenestrae to allow passage of nutrients, etc. However, in most tissues these pores are too small—about 4 nm diameter—to normally allow extravasation of many potentially therapeutic molecules including polynucleotides. In addition, potentially therapeutic cationic molecules have poor biodistribution because of electrostatic interactions with negatively charged serum components. Using the described processes, extravasation of fluid and molecules out of coronary vessels and delivery to cells of the surrounding heart tissue is increased.

The described delivery system comprises an intravascular administration route. Blood vessels comprise internal hollow tubular structures connected to a tissue or organ within the body of an animal, including a mammal. Blood flows to or from the body part within the lumen of the tubular structure. Blood vessels comprise: arteries, arterioles, capillaries, venules, sinusoids and veins. Afferent vessels are directed towards the organ or tissue and in which fluid flows towards the organ or tissue under normal physiological conditions. Conversely, efferent vessels are directed away from the organ or tissue and in which fluid flows away from the organ or tissue under normal physiological conditions. Intracoronary refers to an intravascular route for delivery to the heart wherein the blood vessels are the coronary arteries and veins. In the heart, afferent vessels are known as coronary arteries, while efferent vessels are referred to as coronary veins. Accessible vessels in the heart may be selected from the list comprising: aorta, coronary sinus, great cardiac vein, inferior vena cava, left anterior descending artery, left anterior descending diagonal artery, left circumflex artery, left circumflex obtuse marginal artery, left main coronary artery, middle cardiac vein, obtuse marginal artery, posterior descending artery, posterior lateral artery, pulmonary arteries and veins, right coronary artery and superior vena cava. A vascular network consists of the directly connecting vessels supplying and/or draining fluid in a target organ or tissue. Raising the intravascular hydrostatic pressure transiently increases fluid flow through the vessel walls thereby enabling extravasation of the polynucleotide.

Experiments in pig heart demonstrate that cardiac tissue can be efficiently transfected following rapid injection of plasmid DNA in an appropriate volume of saline or other pharmacologically acceptable solution into a vessel of the heart. Transfection efficiency (as determined by luciferase expression) appeared equally efficient following injection into coronary arteries or veins. Most importantly, a retrograde approach, in which the plasmid DNA was delivered to heart muscle cells from the coronary vein, was as efficient as injection through the arteries. This observation indicates that the delivery process would be useful in patients with occluded coronary arteries. Retrograde intravenous delivery avoids the potential problem of loosening and dislodging plaques associated with catheters advanced in coronary arteries.

In the examples provided, we demonstrate that small polynucleotides can be efficiently delivered to heart tissue cells. The delivered polynucleotides (siRNA for example) are effective in inhibiting expression of target genes in the heart cells.

Delivery of siRNA or other polynucleotides to heart tissue in order to inhibit gene expression can be done for both therapeutic and research purposes. Potential target genes for RNAi treatment include, but are not limited to: lamin A/C (multiple mutations cause different laminopathies, e.g., dilated cardiomyopathy), JAG1 gene for treatment of Alagille syndrome, cardiac sodium channel genes for treatment of (progressive) cardiac conduction defects, sarcolemmal sodium/calcium exchanger for enhancement of cardiac contractility (activity is elevated in heart failure), and fibrillin 1 (FBN1) for treatment of Marfan syndrome. Each of these defective genes has a dominant negative phenotype. Therefore, inhibition of the defective gene will have a therapeutic effect. Inhibition of normal genes in model animals can serve to aid in the study of the function of the targeted gene.

For intravascular polynucleotide delivery to the heart, the volume of the delivery solution and the rate of injection of the solution are important to achieve good delivery. The choice of injection volume and rate are dependent upon: the size of the animal, the size of the vessel into with the solution is injected, the size and or volume of the target tissue, the bed volume of the target tissue vasculature, and the nature of the target tissue or vessels supplying the target tissue. Larger injection volumes and/or higher injection rates are typically required for a larger vessels, target sizes, etc. Injection rates can vary from 0.5 ml/sec or lower to 9.7 ml/sec or higher. For delivery of polynucleotides to heart cells via the left anterior descending artery or vein in pig, injection volumes of 15-30 ml are effective. Occlusion of vessels, by balloon catheters, clamps, natural occlusion, etc, can limit or define the vascular network size or target area.

The coronary vasculature in the circumflex is not anatomically identical from one individual to another. Moreover, a single bed (defined as artery into microcapillary bed into vein) may be connected to other beds by collateral flow. In other words, the target bed size in the heart will vary from case to case. In order to correlate variations in the injection parameters with delivery efficiency, determination of the bed size may be important. This determination can be done by injection of iodinated contrast dye detected by fluoroscopy. By performing this procedure prior to injection, gene transfer efficiency can be expressed per total target bed size. It also allows for prediction of the required injection volume and speed. In one preferred embodiment (i.e., polynucleotide extravasation and myocyte transfection), a threshold volume in a set time is exceeded and then maintained for a short time. This will form a square wave form on a plot of intravenous volume versus time. To reach the threshold, a larger injection volume or higher injection speed is required for a larger target bed. Therefore, an automatic injection system can be used to inject the polynucleotide solution such that this pressure threshold is reached and then maintained at or above this threshold for a given time. By creating a feedback between the intravascular pressure at the site of injection and the injection pump, a system can be created that automatically senses the target bed size and injects the proper amount of transfection solution. By limiting the injection volume per time unit and intravascular pressure, minimal tissue damage is incurred.

Our experiments demonstrate that efficient delivery to cardiac tissue cells can be obtained by injection of polynucleotide into a heart vein (or artery) without preventing blood flow through the corresponding artery (or vein). It seems that the microcapillary bed generates sufficient resistance to elevate intraluminal pressure during the injection to enable polynucleotide extravasation and delivery to cardiac cells. It is well known that the postcapillary venous endothelium allows the highest rates of fluid and macromolecule transport. In ischemic heart, blocked arteries may help to occlude fluid flow and enhance vessel permeability to polynucleotides during the delivery process.

The permeability of a blood vessel may be further increased by increasing the osmotic pressure within the blood vessel. Typically, hypertonic solutions containing salts such as sodium chloride, sugars or polyols such as mannitol are used. Hypertonic means that the osmolality of the injection solution is greater than physiologic osmolality. Isotonic means that the osmolality of the injection solution is the same as the physiological osmolality (i.e., the tonicity or osmotic pressure of the solution is similar to that of blood). Hypertonic solutions have increased tonicity and osmotic pressure compared to the osmotic pressure of blood and cause cells to shrink.

The permeability of the blood vessel can also be increased by a biologically-active molecule such as a protein or a simple chemical (such as histamine) that increases the permeability of the vessel by causing a change in function, activity, or shape of cells within the vessel wall such as the endothelial or smooth muscle cells. An examples of such a molecule is vascular permeability factor (VPF) which is also known as vascular endothelial growth factor (VEGF). Another type of biologically active molecule can increase vessel permeability by changing the extracellular connective material of the vessel. For example, an enzyme could digest the extracellular material and increase the number and size of the holes of the connective material. Other biologically active molecules that may alter the permeability include calcium channel blockers (e.g., verapamil, nicardipine, diltiazem), beta-blockers (e.g., lisinopril), phorbol esters (e.g., PKC), ethylenediaminetetraacetic acid (EDTA), adenosine, papaverine, atropine, and nifedipine.

Definitions

Polynucleotide—The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. Polynucleotides may contain an expression cassette coded to express a whole or partial protein, or RNA. An expression cassette refers to a natural or recombinantly produced polynucleotide that is capable of expressing a sequence. The term recombinant as used herein refers to a polynucleotide molecule that is comprised of segments of polynucleotide joined together by means of molecular biological techniques. The cassette contains the coding region of the gene of interest along with any other sequences that affect expression of the sequence of interest. An expression cassette typically includes a promoter (allowing transcription initiation), and a transcribed sequence. Optionally, the expression cassette may include, but is not limited to, transcriptional enhancers, non-coding sequences, splicing signals, transcription termination signals, and polyadenylation signals.

The polynucleotide may contain sequences that do not serve a specific function in the target cell but are used in the generation of the polynucleotide. Such sequences include, but are not limited to, sequences required for replication or selection of the polynucleotide in a host organism.

The term naked polynucleotide indicates that the polynucleotide is not associated with a transfection reagent or other delivery vehicle that is required for the nucleic acid or polynucleotide to be delivered to the cell. A transfection reagent is a compound or compounds that bind(s) to or complex(es) with oligonucleotides and polynucleotides, and mediates their entry into cells. The transfection reagent also mediates the binding and internalization of oligonucleotides and polynucleotides into cells. Examples of transfection reagents include, but are not limited to, cationic lipids and liposomes, polyamines, calcium phosphate precipitates, histone proteins, polyethylenimine, and polylysine complexes. It has been shown that cationic proteins like histones and protamines, or synthetic cationic polymers like polylysine, polyarginine, polyornithine, DEAE dextran, polybrene, and polyethylenimine may be effective intracellular delivery agents. Typically, the transfection reagent has a net positive charge that binds to a polynucleotide's negative charge. The transfection reagent mediates binding of polynucleotides to cells via its positive charge (that binds to the cell membrane's negative charge) or via cell targeting signals that bind to receptors on or in the cell. For example, cationic liposomes or polylysine complexes have net positive charges that enable them to bind to DNA or RNA.

Functional RNA: A functional RNA comprises any RNA that is not translated into protein but whose presence in the cell alters the endogenous properties of the cell.

Polynucleotide-based gene expression inhibitor. A polynucleotide-based gene expression inhibitor comprises any polynucleotide or nucleic acid analog containing a sequence whose presence or expression in a cell causes the degradation of or inhibits the function, transcription, or translation of a gene or its transcribe RNA in a sequence-specific manner. Inhibition of RNA can effectively inhibit expression of a gene from which the RNA is transcribed. Polynucleotide-based gene expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (mRNAs) are small noncoding polynucleotides, about 22 nucleotides in length, that direct destruction or translational repression of their mRNA targets. If the complementarity between the mRNA and the target mRNA is partial, then translation of the target mRNA is repressed, whereas if complementarity is extensive, the target mRNA is cleaved. Antisense RNAs comprise sequence that is complimentary to an gene sequence or mRNA sequence. Antisense polynucleotides include, but are not limited to: morpholinos, 2'-O-methyl polynucleotides, DNA, RNA and the like. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters. These DNAs can be delivered to a cell wherein the DNA is transcribed to produce small hairpin siRNAs, separate sense and anti-sense strand linear siRNAs, or RNAs that can function as antisense RNA or ribozymes.

The polynucleotide-based gene expression inhibitor may be polymerized in vitro, recombinant RNA, contain chimeric sequences, or derivatives of these groups. The polynucleotide-based gene expression inhibitor may contain ribonucleotides, deoxyribonucleotides, synthetic nucleotides, or any suitable combination such that the target RNA and/or gene is inhibited.

Delivery of a polynucleotide means to transfer the polynucleotide from a container outside a mammal to near or within the outer cell membrane of a cell in the mammal. The term transfection is used herein, in general, as a substitute for the term delivery, or, more specifically, the transfer of a polynucleotide from directly outside a cell membrane to within the cell membrane. A delivery system is the means by which a biologically active compound becomes delivered. That is all compounds, including the biologically active compound itself, that are required for delivery and all procedures required for delivery including the form (such as volume) and method of administration.

Permeability is defined herein as the propensity for macromolecules such as polynucleotides to move through vessel walls and enter the extravascular space. One measure of permeability is the rate at which macromolecules move through the vessel wall and out of the vessel. Another measure of permeability is the lack of force that resists the movement through the vessel wall and out of the vessel. Vessels contain elements that prevent macromolecules from leaving the intravascular space (internal cavity of the vessel). These elements include endothelial cells and connective material (e.g., collagen). Increased permeability indicates that there are fewer of these elements that can block the egress of macromolecules and/or that the spaces between these elements are larger and more numerous. In this context, increased permeability enables a higher percentage of macromolecules being delivered to leave the intravascular space, while low permeability indicates that a low percentage of the macromolecules will leave the intravascular space.

The permeability of a blood vessel can be increased by increasing the intravascular hydrostatic pressure. The intravascular hydrostatic pressure can be increased by rapidly (from 1 second to 30 minutes) injecting a nucleic acid in solution into the blood vessel. Hydrostatic pressure can also be increased by obstructing the outflow of the injection solution from the tissue for a period of time sufficient to allow delivery of a polynucleotide. Obstructing means to block or impede the outflow of injection fluid, thereby transiently (reversibly) blocking the outflow of the blood. Furthermore, rapid injection may be combined with obstructing the outflow in yet another preferred embodiment. For example, an afferent vessel supplying an organ is rapidly injected while the efferent vessel draining the tissue is blocked transiently (e.g., by ligation, or by an inflated intravascular balloon). The efferent vessel (also called the venous outflow or tract) draining outflow from the tissue is partially or totally clamped for a period of time sufficient to allow delivery of a nucleic acid. In the reverse, an efferent vessel is injected while the corresponding afferent vessel is occluded.

The terms therapeutic and therapeutic results are defined in this application as levels of gene products or gene suppression, including reporter (marker) gene products, which indicate a reasonable expectation of gene expression or inhibition using similar polynucleotides, at levels considered sufficient by a person having ordinary skill in the art of gene therapy. For example: Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. This indicates that in severe patients only 2% of the normal level can be considered therapeutic. Levels greater than 6% prevent spontaneous bleeds but not those secondary to surgery or injury. A person having ordinary skill in the art of gene therapy would reasonably anticipate therapeutic levels of expression of a gene specific for a disease based upon sufficient levels of marker gene results. In the Hemophilia example, if marker genes were expressed to yield a protein at a level comparable in volume to 2% of the normal level of factor VIII, it can be reasonably expected that the gene coding for factor VIII would also be expressed at similar levels.

EXAMPLES

The following examples are intended to illustrate, but not limit, the present invention.

Example 1

SiRNA is Efficiently Delivered to Cardiac Muscle Cells and Inhibits Gene Expression Following Intravascular Delivery Animal #1 and #2—Pigs were injected with plasmids and siRNA known to inhibit expression of the gene expressed from the plasmid. The injection solution was prepared by adding 100 µg/ml each of plasmids encoding either Firefly luciferase or *Renilla* luciferase genes as well as 45 µg/ml of Firefly-specific siRNA, siRNA-luc$^+$. Control animals were injected with plasmid only (no siRNA present). The injection solution was saline with 2.5 mg/ml lidocaine. The injection volume was 20 ml and the rate of injection was 5.0 ml/second. Injection was done by retrograde instillation into the left anterior descending vein using a balloon catheter. The animals were sacrificed 48 h after injection and the heart was excised. Tissue specimens (approximately 1 gram each) were obtained from the heart tissue perfused by the left anterior descending vessel vasculature (i.e. from the muscle surrounding the left anterior descending artery and vein). Specimens were frozen in liquid nitrogen and stored at −80° C. Expression levels were measured by preparing homogenates and measuring activity of the firefly luciferase$^+$ and the renilla luciferase using a commercial available assay kit (Promega). Data is expressed as a ratio fireflyluc$^+$/renillaluc.

Animal #3 and #4—This animal was injected with plasmids only. The injection solution was prepared by adding 100 µg/ml each of Fireflyluc$^+$ and Renillaluc to a saline solution which also contained 2.5 mg/ml of lidocaine. The injection volume was 12.5-16 ml and the rate of injection was 4.5-6 ml/second. Injection was done by retrograde instillation into the left anterior descending vein using a balloon catheter. The animal was sacrificed 48 h after injection and the heart was excised. Tissue specimens (approximately 1 gram each) were obtained from the heart tissue perfused by the left anterior descending vessel vasculature (i.e. from the muscle surrounding the left anterior descending artery and vein). Specimens were frozen in liquid nitrogen and stored at −80° C. Expression levels were measured by preparing homogenates and measuring activity of firefly luciferase$^+$ and the renilla luciferase using a commercial available assay kit (Promega). Data is expressed as a ratio fireflyluc$^+$/renillaluc.

The data, shown in Table 1 and Table 2, show that siRNA was efficiently delivered to heart muscle cells near the left anterior descending artery and vein vasculature following retrograde injection of a solution containing the siRNA into the left anterior descending vein. In animals receiving siRNA, firefly luciferase expression was reduced 70-90% (ratio of firefly luciferase to Renilla luciferase in control vs. siRNA animals). Co-delivery of siRNA with a plasmid containing an expressible reporter gene was used as a convenient method to quantitatively assay delivery of the siRNA. The invention does not require co-delivery of a plasmid for delivery of siRNA. The absence of plasmid DNA in the injection solution does not effect siRNA delivery. Each value for animal #4 represents the average of two samples.

TABLE 1

Delivery of siRNA to cardiac muscle cells via retrograde instillation into the left anterior descending vein

|  | Luciferase Activity (RLUs) | | Firefly/ |
|---|---|---|---|
|  | Renilla | Firefly | Renilla |
| animal #1 | 2,606,023 | 45,255 | 0.017 |
|  | 1,865,868 | 41,435 | 0.022 |
|  | 1,009,623 | 25,600 | 0.025 |
|  | 123,958 | 6,385 | 0.052 |
|  | 293,653 | 755 | 0.003 |
|  | 23,148 | 320 | 0.014 |
|  | 76,803 | 945 | 0.012 |
| average | 857,010 | 17,242 | 0.020 |
| total | 5,999,073 | 120,695 |  |
| animal #2 | 183,465 | 21,350 | 0.12 |
|  | 990,065 | 38,630 | 0.039 |
|  | 120,695 | 9,580 | 0.079 |
|  | 7,505 | 2,265 | 0.30 |
|  | 39,650 | 11,380 | 0.29 |
|  | 108,645 | 5,325 | 0.049 |
|  | 15,635 | 1,465 | 0.094 |
|  | 15,155 | 1,055 | 0.070 |
|  | 12,585 | 2,145 | 0.17 |
|  | 16,175 | 1,275 | 0.079 |
|  | 170,635 | 8,630 | 0.051 |
|  | 13,840 | 2,580 | 0.19 |
| average | 141,171 | 8,807 | 0.062 |
| total | 1,694,050 | 105,680 |  |

TABLE 2

Renilla and Firefly luciferase expression in control animals not receiving firefly-specific siRNA.

|  | Luciferase Activity (RLUs) | | Firefly/ |
|---|---|---|---|
|  | Renilla | Firefly | Renilla |
| animal #3 | 75,923 | 304,450 | 4.01 |
| no siRNA control | 501,513 | 1,033,850 | 2.06 |
|  | 199,222 | 472,570 | 2.37 |
|  | 9,283 | 19,580 | 2.11 |
|  | 12,202 | 7,460 | 0.61 |
|  | 316,663 | 603,570 | 1.91 |
|  | 90,412 | 103,980 | 1.15 |
|  | 628,963 | 1,150,540 | 1.83 |
|  | 118,152 | 211,310 | 1.79 |
|  | 73,843 | 83,680 | 1.13 |

TABLE 2-continued

Renilla and Firefly luciferase expression in control animals not receiving firefly-specific siRNA.

|  | Luciferase Activity (RLUs) | | Firefly/ |
|---|---|---|---|
|  | Renilla | Firefly | Renilla |
|  | 9,133 | 10,220 | 1.12 |
|  | 16,682 | 16,980 | 1.02 |
|  | 22,112 | 40,930 | 1.85 |
|  | 142,813 | 226,130 | 1.58 |
|  | 120,072 | 263,610 | 2.20 |
|  | 19,272 | 39,420 | 2.05 |
|  | 41,033 | 72,440 | 1.77 |
| average | 141,017 | 274,160 | 1.94 |
| total | 2,397,293 | 4,660,720 | |
| animal #4 | 15656 | 33905 | 2.21 |
| no siRNA control | 20501 | 55155 | 2.69 |
|  | 34148 | 104293 | 3.04 |
|  | 50838 | 154645 | 2.99 |
|  | 979421 | 3005915 | 2.89 |
|  | 4127548 | 13391003 | 3.23 |
|  | 5773616 | 18548940 | 3.20 |
|  | 7232438 | 25413183 | 3.50 |
|  | 9061823 | 32462075 | 3.59 |
|  | 17620838 | 68046103 | 3.88 |
| average | 4491683 | 16121522 | 3.12 |
| total | 44916825 | 161215215 | |

Example 2

In vivo Luciferase Expression from Naked Plasmid DNA Transfected to A Pig Heart

Solutions of pCI-Luc+ were injected into coronary arteries and veins in pig heart. pCI-Luc+ is a plasmid DNA expression vector in which an optimized version of the firefly luciferase gene (Promega, Madison, Wis.) is expressed under transcriptional control of the CMV promoter (basic expression vector is pCI, Promega, Madison, Wis.). The hearts of 30-40 kg domestic pigs were accessed via a limited left thoracotomy through the fifth intercostal space. A 27-gauge needle was inserted into a left anterior descending (LAD, great cardiac) or right posterior descending (middle cardiac) vein or artery, and ligated in place. The ligation serves to keep the needle in place and to direct flow distal from the needle. The corresponding artery or vein was transiently occluded during the injection. A pre-injection into the coronary artery or vein of 6 ml papaverine solution (0.5 mg/ml) was given in 15-20 seconds. After 5 minutes, a 30 ml solution of 50 µg/ml plasmid DNA in saline with 15% mannitol (w/v) was injected in ~20-30 seconds. Following injection, the ligation and needle were removed, bleeding stopped, and the pericardium and chest closed. In most pigs, the LAD bed and a site in the circumflex were injected. In two pigs, direct interstitial injections were also performed for comparison.

48 h after injection, the animals were sacrificed and sections from the injection site were excised and assayed for reporter gene expression. Sections from the heart (ca. 1.5 gram each) were homogenized in a Triton X-100 lysis buffer. Luciferase activity was measured with an Analytical Luminescence Laboratories luminometer. Activity levels are expressed as the amount of luciferase protein per gram of heart tissue. Plasmid DNA was obtained from BayouBioLabs (Harahan, La.) and was supercoiled purified and endotoxin free.

Luciferase expression in the area around the injection site averaged 26.2 ng/g tissue (range 2.3-61.8; n=5). Both arterial and venous delivery resulted in efficient luciferase expression. In one animal, we compared intravenous delivery while transiently occluding the corresponding artery with leaving arterial flow open. Luciferase expression levels were 7.22 vs. 7.76 ng/g, respectively. This suggests that the capillary bed itself accounts for sufficient resistance to retrograde flow to increase vascular permeability above the required threshold for efficient plasmid DNA extravasation.

Direct interstitial injection of 500 µg plasmid DNA in 500 µl saline resulted in an average expression level of 70.3 ng luciferase per gram tissue (range 9.6-115.2; n=3). Expression appeared far more limited to the area of injection. Analysis of tissues around the injected bed after intravascular delivery, showed lower levels of expression extending to relatively distant sites.

All of the pigs injected recovered well from the procedure, and little damage was observed. Tissue sections from the injection site and stained with hematoxylin-eosin did not show any major histological abnormalities.

Example 3

Retrograde Cardiac Venous Gene Delivery

Pigs (30-50 kg) of either sex were anesthetized with Telazol (tiletamine HCl and zolazepam HCl, 4-5 mg/kg IM) and thiopental (7-9 mg/kg IV), intubated and mechanically ventilated. Anesthesia was maintained with inhaled isoflurane (0.5%-1.5%). The right carotid artery was exposed via a midline incision and cannulated with an 8-9 Fr introducer sheath. A 10.5-11 Fr sheath was placed in the right jugular vein. The left main coronary artery was engaged with a coronary angiographic catheter and a left coronary artery angiogram was obtained. A modified 10 Fr guiding catheter was advanced through the jugular sheath into the coronary sinus. The delivery catheter (modified triple-lumen 7 Fr balloon-tipped pulmonary artery catheter with an infusion lumen, a balloon inflation/deflation lumen and an end-hole lumen for intravascular pressure measurements) was advanced over a guidewire into the proximal great (anterior) cardiac vein. The vein was occluded by inflating the latex balloon on the distal tip of the catheter. Low pressure injections of diluted iodinated contrast were used, in conjunction with the left coronary angiogram, to delineate the myocardial territory drained by the vein. Retrograde infusions of 15-30 ml of pDNA solution were performed in 17 pigs using an injection pump (MedRad, Inc., Pittsburgh, Pa.) at constant flow rates (3-7 ml/sec). In injections resulted in a rapid rise in coronary intravenous pressure to a mean injection pressure of 804±242 mmHg (range 515-1225 mm Hg). No ventricular tachycardia was observed during the 11 experiments were the mean injection pressure was less than 1000 mm Hg. The occlusion balloon was left inflated for 2 min following the injection. Following gene delivery, both vessels were ligated and the neck incision was closed. In some animals, 6 ml of a 0.5 mg/ml papaverine solutions was injected 5 minutes prior to plasmid DNA delivery.

Total luciferase expression in the heart 48 hours after transfection with this method was 673±587 ng (range 18 to 2,124 ng), with peak expression of luciferase in the anterior wall of 118±113 ng luciferase per gram heart tissue (range 4.4-455 ng/g). Luciferase expression was typically observed in the entire anterior and anteroseptal walls of the left ventricle. For the 8 experiments where the mean intravenous injection pressure was between 500 and 700 mm Hg, total luciferase expression was 624±663 ng (range 18-2024 ng).

For comparison, direct intramyocardial injections were performed. For these injections, the heart was exposed via a fourth interspace left thoracotomy and 0.5 ml of pDNA solution was directly injected in the lateral wall of the left ventricle using a 25 gauge needle. Following pDNA injections, the pericardium was closed, the ribs approximated, and the muscles and skin were closed by individual layers. Direct intramyocardial injection of 500 µg pCI-Luc$^+$ at 5 sites in 3 separate pigs resulted in a total luciferase expression of 16.8±8.4 ng in the myocardium at each injection site, with peak expression of 9.6±8.4 ng/g myocardium. Luciferase expression was limited to a relatively small area of myocardium immediately adjacent to the injection site.

Example 4

Estimation of the Number of Transfected Cardiomyocytes Following Plasmid DNA Delivery Into a Cardiac Vein Intravenous injection of pCI-LacZ was performed to determine the cell type and extent of transfection. Crysosections (10 µm) were stained for β-galactosidase expression as described before. A low percentage of transfected cardiomyocytes was detected two days following injection. No endothelial cells were found to express β-galactosidase. The percentage of β-galactosidase positive cells appears rather low for the amount of luciferase expression that was found in the same tissue samples (15 ng/g, generated by ~10-fold less pCI-Luc$^+$ than was used in the experiments describe in example 1; in this experiment, pCI-Luc$^+$ was co-injected with pCI-LacZ at a ratio of 1:9). The same tissue sections were also stained with hematoxylin-eosin. No gross abnormalities were observed.

Example 5

Plasmid DNA Delivery to Coronary Veins Via a Catheter

Gene transfer experiments were performed in 30-50 kg Yorkshire domestic swine (Sus scrofa). The pigs were sedated with telezol (20-30 mg IM), induced with pentobarbitol (250-500 mg IV), and endotracheally intubated. Anesthesia was maintained with inhaled isoflurane (0.5-3%). The right carotid artery and internal jugular vein were exposed by surgical cutdown and coronary angiography was performed. Heparin (100 U/kg, IV) was administered. A 10 Fr guiding catheter was advanced to the coronary sinus, and a 7 Fr balloon-tipped triple lumen catheter was advanced over a 0.014 inch guidewire into the cardiac vein draining the left anterior descending (great cardiac vein) or right posterior descending (middle cardiac vein) territories. Low pressure injections of diluted iodinated contrast were used, in conjunction with the coronary angiogram, to delineate the myocardial territory drained by each vein.

The larger lumen of the balloon-tipped triple lumen catheter is used for fluid injection, while the smaller lumen is used to monitor cardiac vein pressures during plasmid DNA infusion; the third lumen is used to inflate and deflate the balloon. Following placement of the catheter, the balloon was inflated, and 6 ml saline or 6 ml saline with 3 mg papaverine was instilled through the large lumen (which opens distal to the balloon). The installation required 3-20 seconds and resulted in slightly increased venous pressure (10-350 mmHg). After 5 minutes, the balloon was deflated for 20-30 seconds and then inflated again followed by plasmid DNA delivery. A saline solution containing 100 µg/ml pCI-Luc$^+$ was rapidly delivered through the main lumen. During the injections of 25-30 ml plasmid DNA solution in 8-20 seconds, the intravenous pressure increased (120-500 mmHg). In some pigs, two sites were injected (one in the posterior descending, the other in the left anterior descending territory); in other pigs, only one site was injected (left anterior descending).

Two days following injection, the animals were sacrificed, the heart excised, divided in 1-2 gram sections, and assayed for reporter gene expression. Maximum expression levels (near the site of plasmid DNA delivery) varied from 1.4 to 456.9 ng luciferase per gram of heart tissue (n=8).

|  | Experiment | Peak luciferase expression (ng luciferase per gram tissue) |
|---|---|---|
| Single-lumen catheters | 1 | 456.9 |
|  | 2 | 370.8 |
|  | 3 | 1.39 |
| Multi-lumen catheters | 4 | 4.01 |
|  | 5 | 2.38 |
|  | 6 | 5.86 |
|  | 7 | 167.24 |
|  | 8 | 2.25 |
|  | 9 | 0.15 |
|  | 10 | 48.03 |
|  | 11 | 12.40 |
|  | 12 | 0.48 |
|  | 13 | 5.29 |

Example 6

Modified Catheter

A 10F guide catheter was shortened to 50-60 cm (from 100 cm). The bend was adjusted as needed. The injection catheter is shortened to 80-90 cm down from 135 cm. A 2 cm portion of the tip end was shaved by 0.005-0.009 inch to accommodate the thin walled silastic balloon that is fabricated on the narrowed portion. A fluid-filled catheter was inserted in the large lumen to measure the infusion pressure.

Example 7

Modified Two-lumen Catheter

A custom, double-lumen balloon angioplasty catheter and an angioplasty guidewire with micro-miniaturized piezo pressure-transducer elements to measure venous bed pressures during injections, can be used as a more practical and convenient alternative.

Example 8

Modified Three-lumen Catheter

A triple-lumen balloon angioplasty catheter can be used to accommodate polynucleotide delivery, control of balloon, and a fluid-filled lumen for pressure measurements.

Example 9

Automated Injection System

An automated injection system was constructed to provide reproducible and consistent delivery of nucleic acid solutions. The system consists of a Macintosh PowerBook G3 laptop computer (Apple Computer, Cupertino, Calif.), a DAQCard AI-16E-4 data acquisition input and output system (National Instruments, Austin, Tex.), and LabView software (National Instruments). The intravenous pressure (distal to the inflated balloon catheter) is measured, using a pressure transducer guidewire or a fluid-filled lumen attached to a pressure transducer. The pressure transducer is coupled to the DAQCard, the signal digitized and read into the custom control program (made in LabView). The pressure reading is compared to a preset target value. The control program can directly influence the speed of injection of the power injector. A pressure value below the preset would result in an increase in the injection rate; a pressure value above the preset would result in a decrease in the injection rate. The control software allows for regulation of maximum increases/decreases in injection rate in order to prevent extremely fast ramping or oscillations. It also allows for control of maximum injection volume. In another embodiment, the system will also measure other clinical relevant parameters (heart rate, oxygen saturation level, breathing/ventilation rate, etc.), as to provide information on these procedure related variables.

Example 10

Feedback Control of Intravascular Injection Pressures

To achieve more precise control of intravascular pressures during plasmid infusions, a feed-back controlled infusion system was developed. Intravenous pressures were monitored during solution injections as before using a fluid-filled lumen of the injection catheter and a Gould P23IV pressure transducer (Gould). A voltage-regulated infusion pump (ACIST Medical, Minneapolis, Minn.) was controlled by an Apple Powerbook laptop computer using custom software (LabView, National Instruments, Austin, Tex.) and a PCMCIA AD/DA converter. Because of phase delays resulting from the fluid-filled pressure monitoring lumen, the larger infusion lumen of the infusion catheter and the compliance of the coronary venous system, a complex algorithm including feed-forward as well feed-back relationships was developed to effectively clamp coronary intravenous pressures to a desired level during plasmid infusions.

Figure 1A:
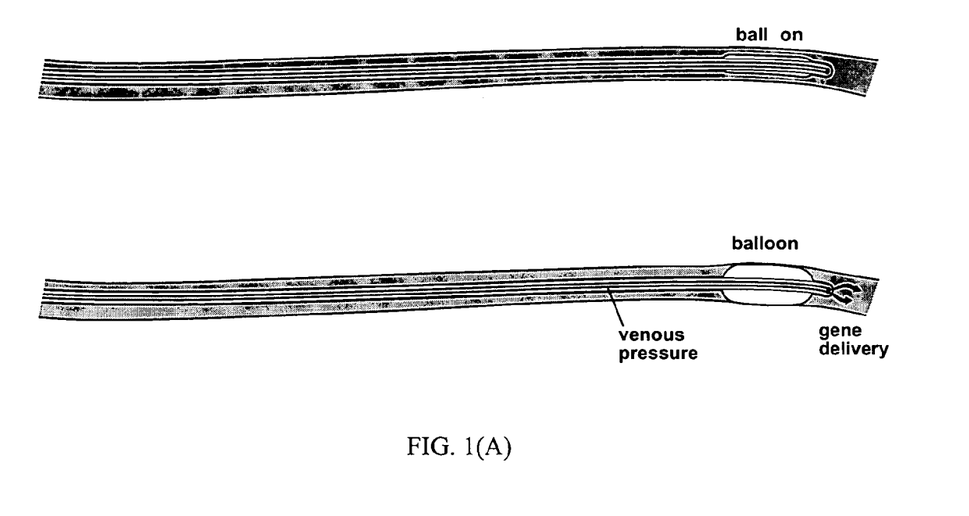
Figure 1B:
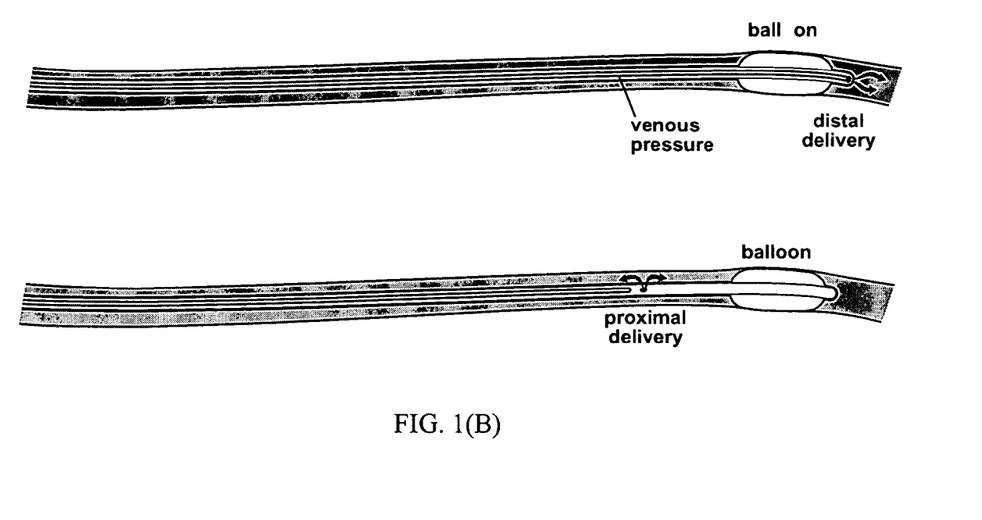
Figure 2:
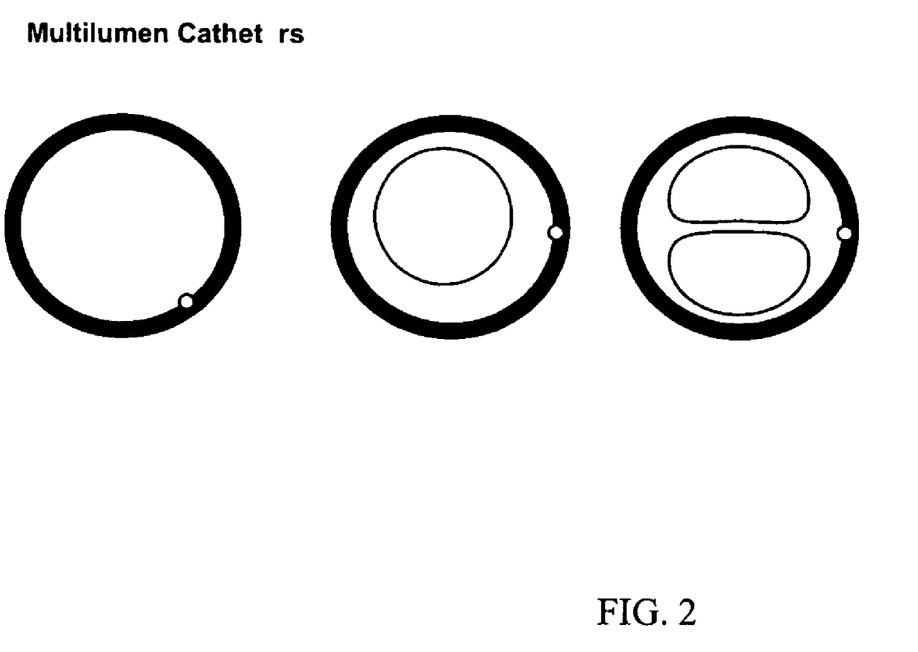
FIG. 2. Multilumen catheters for nucleic acid delivery: Catheters can be made with multiple lumens that can be accessed independently. For instance, catheters with 2, 3, or 4 lumens are diagrammed. The individual lumens can be of similar size, or of different size. In this diagram, catheters with unequal sized lumens are shown. Multiple lumen catheters can be used to perform several functions simultaneously. For instance, the three-lumen catheter could be used to deliver a nucleic acid solution through the largest sized lumen, controlling a balloon through another lumen, and use the third lumen for real time pressure measurements (e.g., using a guidewire incorporating a pressure transducer).
Figure 3:
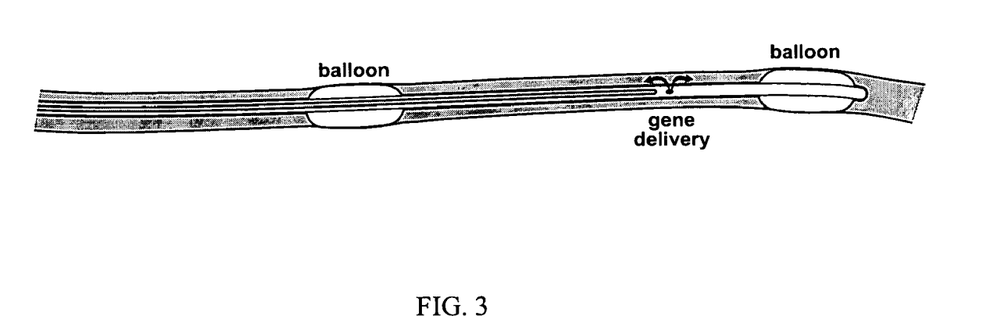
FIG. 3. Double balloon catheters for nucleic acid delivery: A double balloon catheter generally comprises a two-lumen catheter, in which one lumen is used to inflate or deflate the balloons and the other lumen for other purposes, e.g., guidewires, delivery of fluids, intravascular pressure measurements. The two balloons may also be operated independently, by including another lumen. Such catheters are available in many different sizes (diameter, length, distance between the two balloons), to accommodate applications in different sized and localized vessels. In one embodiment, one balloon is located near the tip of the catheter, the other balloon some distance proximal (e.g., 5 cm). In inflated condition, the two balloons will fix the catheter in place in the targeted vessel. Fluid (e.g., for nucleic acid delivery) can be delivered through a lumen exiting in the area between the two balloons. The inflated balloons prevent flow through the blood vessel outside the area enclosed by the two balloons. In another embodiment, the inflated balloons can restrict fluid delivery outside the region enclosed by the balloons.
Figure 4:
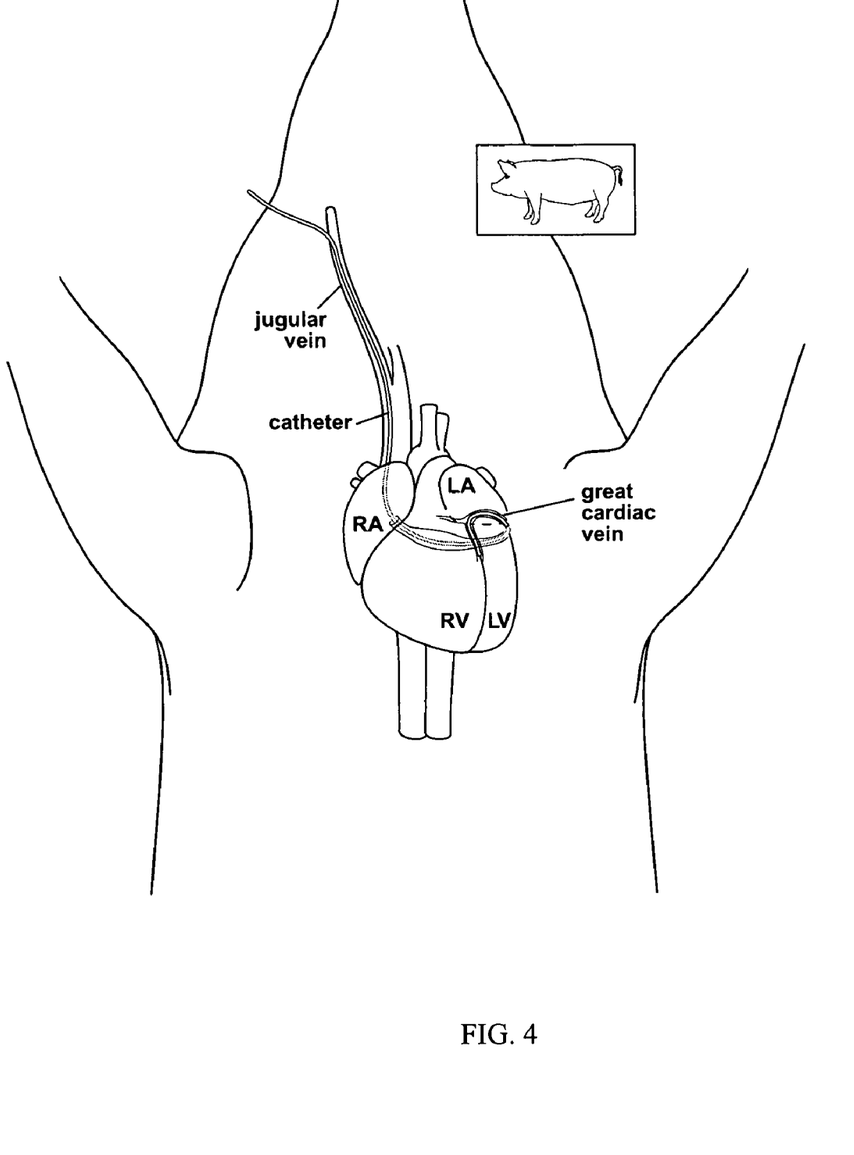
FIG. 4. Nucleic acid delivery to the heart: Nucleic acids are delivered to a specific region of the heart through a catheter. The catheter is advanced into the great cardiac vein via the jugular vein, superior vena cava, right atrium, and coronary sinus. Other areas of the heart can be targeted through other coronary veins (e.g., middle cardiac vein). Alternative nucleic acid routes include delivery through a catheter advanced into a coronary artery, or placement of a needle into a coronary vein or artery (e.g., during open heart surgery or using minimal invasive surgery).

We therefore developed a feed-back controlled infusion pump system to effectively clamp intravenous pressures to less than or equal to 600 mm Hg during DNA infusions (FIG. 4). We observed total luciferase expression of 670 ng in two experiments conducted with this system (480, 861 ng). No ventricular arrhythmias were observed during these experiments.

The foregoing examples are considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering a polynucleotide to a muscle cell in a mammalian heart in a mammal in vivo to inhibit gene expression, comprising:
   a) making a polynucleotide containing a sequence that is substantially complementary to a nucleic acid sequence in the mammal heart cell,
   b) accessing a blood vessel in vivo; and,
   c) inserting a single injector into the blood vessel near or in the heart; and,
   d) injecting a solution containing the polynucleotide into the blood vessel lumen and increasing hydrostatic pressure in the lumen thereby delivering the polynucleotide to the heart muscle cell outside of the blood vessel via the pressure, wherein invasiveness is limited to inserting the single injector into the blood vessel, and injecting the solution.

2. The process of claim 1 wherein increasing hydrostatic pressure in the vessel lumen increases the permeability of the vessel.

3. The process of claim 2 wherein increasing hydrostatic pressure consists of increasing a volume of fluid within the vessel.

4. The process of claim 3 wherein increasing the volume consists of inserting the polynucleotide in solution into the vessel.

5. The process of claim 1 wherein the polynucleotide is selected from the list consisting of: RNA polynucleotide and RNA oligonucleotide.

6. The process of claim 1 wherein injecting the polynucleotide includes injecting the polynucleotide through a catheter.

7. The process of claim 6 wherein injecting the polynucleotide includes injecting a predetermined volume during a predetermined time.

8. The process of claim 7 wherein the polynucleotide is selected from the list consisting of: RNA polynucleotide and RNA oligonucleotide.

9. The process of claim 7 wherein the catheter is inserted into a vessel selected from the list consisting of: aorta, coronary sinus, great cardiac vein, inferior vena cava, left anterior descending artery, left anterior descending diagonal artery, left circumflex artery, left circumflex obtuse marginal artery, left main coronary artery, middle cardiac vein, obtuse marginal artery, posterior descending artery, posterior lateral artery, pulmonary arteries and veins, right coronary artery and superior vena cava.

10. The process of claim 1 wherein the polynucleotide consists of a naked polynucleotide.

11. A process for inhibiting gene expression in mammalian heart muscle cells in a mammal in vivo, comprising:
    a) accessing an blood vessel in vivo;
    b) inserting a single injector into the blood vessel near or in the heart; and,
    c) injecting a solution containing a polynucleotide-based gene expression inhibitor into the blood vessel lumen and increasing permeability of the heart blood vessel thereby delivering the polynucleotide-based gene expression inhibitor to the heart muscle cells outside of the blood vessel via the increased permeability, wherein invasiveness is limited to inserting the single injector into the blood vessel, and injecting the solution.

12. The process of claim 11 wherein injecting the polynucleotide-based gene expression inhibitor includes injecting the polynucleotide-based gene expression inhibitor through a catheter.

13. The process of claim 11 wherein the polynucleotide-based gene expression inhibitor consists is selected from the list consisting of: naked RNA, RNA polynucleotide, and RNA oligonucleotide.

14. The process of claim 11 wherein increasing permeability of the vessel consists of increasing a volume of fluid within the vessel.

15. The process of claim 14 wherein increasing the volume consists of inserting the polynucleotide in solution into the vessel.

16. The process of claim 12 wherein the catheter is inserted into a vessel selected from the list consisting of: aorta, coronary sinus, great cardiac vein, inferior vena cava, left anterior descending artery, left anterior descending diagonal artery, left circumflex artery, left circumflex obtuse marginal artery, left main coronary artery, middle cardiac vein, obtuse marginal artery, posterior descending artery, posterior lateral artery, pulmonary arteries and veins, right coronary artery and superior vena cava.

* * * * *